United States Patent
Wand

(10) Patent No.: US 8,106,674 B2
(45) Date of Patent: Jan. 31, 2012

(54) AUTOMATED LIQUID CRYSTAL ANALYSIS INSTRUMENT

(75) Inventor: Michael Wand, Boulder, CO (US)

(73) Assignee: LC Vision, LLC, Boulder, CO (US)

( * ) Notice: Subject to any disclaimer, the term of this patent is extended or adjusted under 35 U.S.C. 154(b) by 443 days.

(21) Appl. No.: 11/930,455

(22) Filed: Oct. 31, 2007

(65) Prior Publication Data

US 2009/0284262 A1    Nov. 19, 2009

Related U.S. Application Data

(60) Provisional application No. 60/863,761, filed on Oct. 31, 2006, provisional application No. 60/863,765, filed on Oct. 31, 2006.

(51) Int. Cl.
*G01R 31/26* (2006.01)
(52) U.S. Cl. .................................. 324/760.01
(58) Field of Classification Search ............ None
See application file for complete search history.

(56) References Cited

U.S. PATENT DOCUMENTS

| | | | | |
|---|---|---|---|---|
| 3,907,405 A * | 9/1975 | Fukai et al. | ........ | 345/101 |
| 4,128,311 A * | 12/1978 | Smith et al. | ........ | 349/72 |
| 4,278,325 A * | 7/1981 | Kondo et al. | ........ | 349/199 |
| 4,492,107 A * | 1/1985 | Sandhu | ........ | 73/1.83 |
| 5,404,237 A * | 4/1995 | Katsuse et al. | ........ | 349/37 |
| 5,654,207 A * | 8/1997 | Fukuyama et al. | ........ | 204/192.17 |
| 5,684,503 A * | 11/1997 | Nomura et al. | ........ | 345/97 |
| 6,018,378 A * | 1/2000 | Hirai et al. | ........ | 349/89 |
| 6,046,789 A * | 4/2000 | Funfschilling et al. | ........ | 349/172 |
| 6,333,728 B1 * | 12/2001 | Libsch et al. | ........ | 345/90 |
| 7,315,343 B2 * | 1/2008 | Takeoka | ........ | 349/161 |

OTHER PUBLICATIONS

Dahl et al. (1987) "Simple Model for the Polarization Reversal Current in a Ferroelectric Liquid Crystal," *Phys. Rev. A* 36(9):4380-4389.
Escher et al. (Apr. 1988) "Measurement of the Rotational Viscosity of Ferroelectric Liquid Crystals Based on a Simple Dynamic Model," *Liquid Crystals* 3(4):469-484.
Gouda et all. (Jan 1, 1990) "Dielectric Anisotropy and Dielectric Torque in Ferroelectric Liquid Crystals and Their Importance for Electro-Optic Device Performance," *J. Appl. Phys.* 67(1):180-186.
Imai et al. (1994) "Method for Determination of Rotational Viscosity in Nematic Liquid Crystals," *Jpn. J. Appl. Phys.* 33(Part 2, No. 1B):L119-L121.
Patel et al. (May 29, 1987) "The Dependence of the Magnitude of the Spontaneous Polarization on the Cell Thickness in Ferroelectric Liquid Crystals," *Chem. Phys. Lett.* 137:91-95.
Wu et al. (Nov. 1991) "Physical Properties of Chlorinated Liquid Crystals," *Liquid Crystals* 10(5):635-646.

* cited by examiner

*Primary Examiner* — Paresh Patel
(74) *Attorney, Agent, or Firm* — Greenlee Sullivan P.C.

(57) ABSTRACT

Provided is a method for measuring one or more properties of liquid crystals in an automated manner. Also provided is a liquid crystal analysis instrument (LCAS) that automatically measures one or more properties of liquid crystals.

8 Claims, 2 Drawing Sheets

AUTOMATED LIQUID CRYSTAL ANALYSIS INSTRUMENT

CROSS-REFERENCE TO RELATED APPLICATIONS

This application claims priority to U.S. provisional application Ser. Nos. 60/863,761 and 60/863,765, both filed on Oct. 31, 2006, which are hereby incorporated by reference to the extent not inconsistent with the disclosure herein.

BACKGROUND OF THE INVENTION

There is a need in the art for an instrument which analyzes liquid crystal components. Many instruments populate the liquid crystal (LC) analysis market that measure one or several properties of LCs but there are only a few that claim to measure many properties, both electrical and optical, of liquid crystals. Some LC analysis instruments are made by Toyo, Japan, and Instec, USA.

SUMMARY OF THE INVENTION

Provided is a method for measuring one or more properties of liquid crystals in an automated manner. Also provided is a liquid crystal analysis instrument (LCAS) that automatically measures one or more properties of liquid crystals.

More specifically, provided is a method for measuring various properties of liquid crystals comprising: (a) providing a liquid crystal sample; (b) applying one or more of (1) a voltage to the sample; (2) a temperature to the sample; (c) measuring one or more properties of the liquid crystal sample; (d) generating a desired result; and (e) displaying the desired result. The method may optionally include calculating one or more desired values using the measured properties. The voltage may be in the form of a voltage waveform, where the voltage is varied according to a predetermined pattern. The temperature may be in the form of a temperature program, where the temperature is adjusted over time.

DETAILED DESCRIPTION OF THE INVENTION

Figure 1:
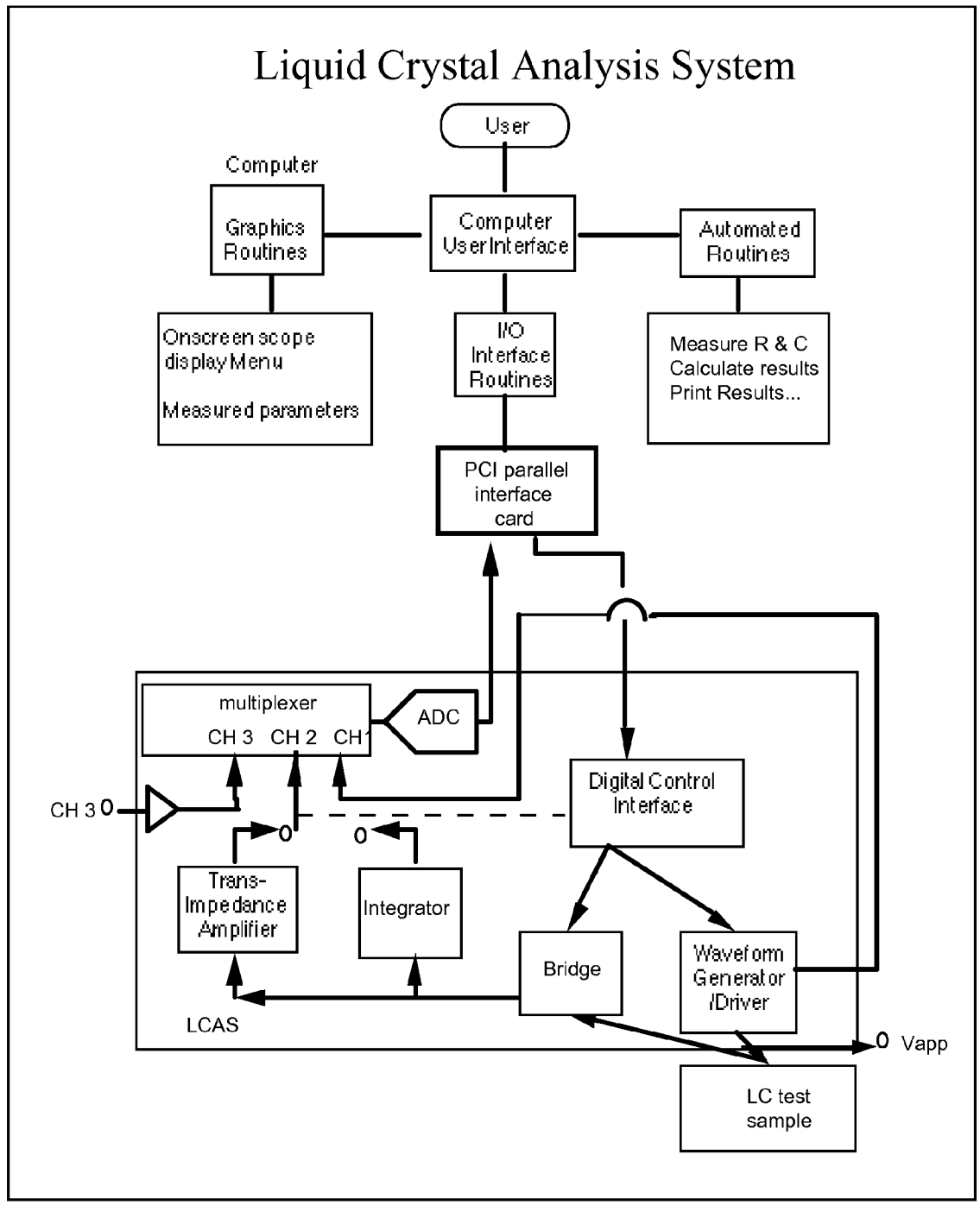
FIG. 1 shows a generalized block diagram of an exemplary LCAS instrument in its most fundamental form. Different amplifiers, A/D converters, and variations in software provide a wide range of useful analysis instruments.
Figure 2:
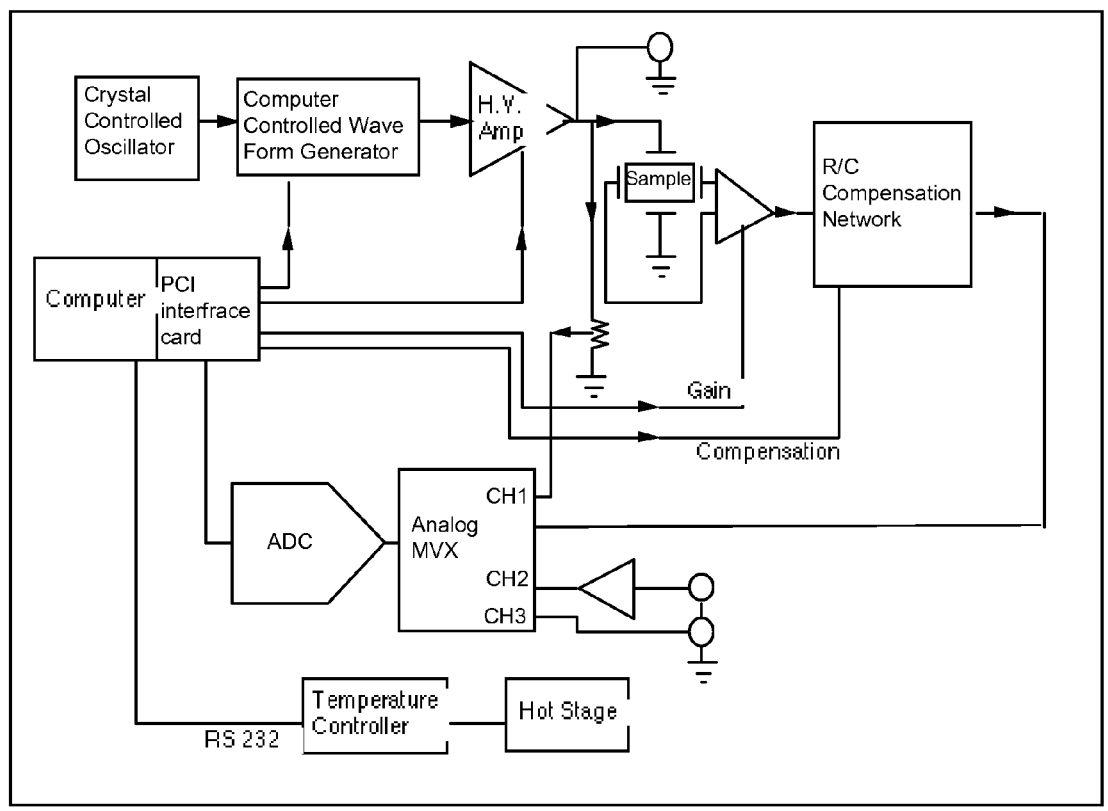
FIG. 2 shows the electronic nature of the LCAS, which shows an example of the electrical flow necessary to accomplish proper measurement of the LC cell.

Provided in one embodiment is an instrument and method for analysis of data associated with liquid crystal components and mixtures. The instrument and methods can be combined in different ways, as further described here.

In one embodiment, one or more of the following features are provided by the Liquid Crystal Analysis System (LCAS):
1. Auto-calibration The system provides auto-calibration against, for example, a known NIST standard. In one embodiment, a commercial surface-mount resistor and capacitor were used and attached to a PCB board for easy connection to the custom cell holder, but any known and verified standard may be used.
2. Statistical Analysis The system provides auto-statistical analysis of the LC being tested. This feature can be set up to run multiple times, from 2 to 1000, more preferably 10 to 20 times. A table of results is generated, in one embodiment. The statistical analysis can be applied to any desired parameter, such as those described here. In one embodiment, one or more of the following parameters are provided:

| Parameter | Mean | St. Dev. | Variance | Min. | Max. | Range |
|---|---|---|---|---|---|---|
| Viscosity | | | | | | |
| Dielectric Constant | | | | | | |
| Resistivity | | | | | | |
| Electrical Rise Time | | | | | | |
| Polarization | | | | | | |
| Number of counts | | | | | | |

All statistical data is calculated using standard equations, for example:

$$\text{Mean} = \frac{\sum P_m}{n}$$

$$\text{Variance} = \frac{\sum (P_m - \text{Mean})^2}{n-1}$$

StdDeviation=$\sqrt{\text{Variance}}$

Range=Max−Min

Where,
$P_m$=value of parameter measured in each test
n=number of tests
Max=maximum value of the parameter for all tests
Min=minimum value of the parameter for all tests Multiple measurements can be made on a given sample to provide the desired statistical significance, or for other reasons. In one embodiment, from 10-20 measurements are used for the statistics. In one embodiment, from 5-1000 measurements are used for the statistics. Other numbers of measurements can be made, as known in the art, to balance time of measurement with statistical significance of the data.

Results can be displayed in many formats, including either jpg (picture) format or els (graphic) format, or ASCI (.doc) format, read by any word processor. Other formats are possible, as known in the art.
3. Phase Diagram The property vs. temperature profile can be used to determine the LC phase diagram of an LC. The most common way to accomplish this is by measuring the heat of enthalpy, or the release or absorption of heat when the sample is cooled or heated, for instance, from its melting point to its clearing point. The method described here requires many fewer sensors and less insulation to accomplish a similar task. By measuring the change in capacitance upon heating or cooling, it is possible to obtain an accurate phase diagram of the LC. Visually examining (or using mathematical analysis) of the resulting curve will provide in a determination of the LC transitions. One embodiment of this method involves locating the area on the curve that most quickly changes, using for example, the first derivative, and more beneficially, the second derivative of the curve and electronically noting the temperature at which this took place. The values are then recorded and reported as an LC transition point, after adjustment with a constant, if necessary. Examples of these transitions are melting point, freezing point, smectic A to nematic, nematic to isotropic, crystal to nematic, smectic C to nematic, smectic C to isotropic, and others.

In one embodiment, one or more of the following parameters are measured or calculated by the LCAS:

Capacitance
Resistance
Thickness
Threshold voltage
Parallel dielectric constant
Perpendicular dielectric constant
Dielectric anisotropy
Splay elastic constant, K11
Twist elastic constant, K2
Rotational viscosity
Bend elastic constant, K33
VHR (voltage holding ratio)
Residual DC voltage
Polarization
Viscosity
Electrical Rise time
Optical Rise time (0-10%, 0-90%, 10-90%)
Bistability
Specific Resistivity
Dielectric Constant
Critical pulse width
Ion density In particular embodiments, any or all of these parameters, including all possible combinations of any or all of these parameters are automatically calculated by the LCAS. The LC properties described here are known in the art.

The following describes one embodiment of using the device and methods. The cell is filled and temperature prepared using standard procedures known in the art. A ferroelectric LC must be filled in the cell when the LC is in the isotropic phase. A nematic LC can be filled in the cell at room temperature. The parasitic capacitance and resistance of the instrument are measured, if needed. The cell's thickness, resistance and capacitance, along with other values if necessary if desired are measured. The test cell's resistance and capacitance are measured ("nulling").

The desired voltage drive waveform frequency and amplitude are selected and applied to the cell, and the desired parameters are measured. The desired temperature profile is selected, and temperature profile is applied to the cell. The desired parameters involving temperature are then measured. Results are calculated using the equations described herein. The data provided by the measurements can be used for perform other measurements. For example, the spontaneous polarization of a single polarization peak can be measured by viewing the polarization peak on a monitor, and using an algorithm to measure the spontaneous polarization. Optical measurements can be made using optical instruments known in the art.

The connections between the cell, temperature source, voltage source and display, as well as other components can be any methods well known in the art. Adjusting the voltage applied, the temperature applied, and other parameters can be done using methods well known in the art. Unless otherwise specified, the units of measurement are usual in the art.

The following are some exemplary equations used to calculate various parameters described here.

Spontaneous Polarization:
The spontaneous polarization (Ps) is calculated as $$Ps = \frac{1}{A_c} \int_o^{\frac{T}{2}} i_p(t) dt$$

where,
Ps=spontaneous polarization
$A_c$=area of the liquid crystal
T=period of test waveform
$I_p(t)$=polarization current
Ps is expressed in $$\frac{nanoColumbs}{centimeter^2}$$

Electrical Rise Time
The electrical rise time is measured from the start of the rising edge of the drive waveform to the peak response of the polarization current. The rise time is expressed in microseconds. The electrical rise time corresponds approximately to the 0% to 50% optical rise time. The more commonly cited 10% to 90% optical rise time will be approximately ⅔ of the electrical rise time.

Applied Electric Field
The electric field is calculated as $$E = \frac{V_P}{d}$$

where,
E=applied electric field
$V_P$=peak voltage of drive waveform
d=cell thickness
The units of the applied electric field are volts per micrometer.

Specific Resistivity
The formula used for calculating the specific resistivity is $$p = \frac{R_M * A_C}{d}$$

where
p=specific resistivity
$R_M$=measured resistance
$A_C$=area of the liquid crystal
d=cell thickness
The specific resistivity is expressed in ohms centimeter.

Dielectric Constant
The dielectric constant is determined from the ratio of the measured capacitances by $$\varepsilon = \frac{C_M - C_P}{C_{EMPTY} - C_P}$$

where
∈=dielectric constant
$C_M$=measured capacitance of the filled test cell
$C_{EMPTY}$=measured capacitance of the empty cell
$C_P$=measured parasitic capacitance
The dielectric constant has no units.

Since non-linear contributions to the dielectric are nulled by the bridge, only the linear dielectric constant is measured and reported. This value is relatively frequency-independent and should be comparable to the unnulled capacitance at high frequencies (>25 KHz). For nematic LCs, the dielectric anisotropy is measured by the single cell method of Wu. For Ferroelectric LCs, the dielectric anisotropy can be obtained by measurement with a parallel-aligned cell. The dielectric constants of the two cells can be used to calculate the dielectric anisotropy.

Ferroelectric Liquid Crystal Rotational Viscosity

The rotational viscosity is found using the following equation $$\eta = \frac{A_C * P_S^2 * V_P}{d * I_P}$$

where
$\eta$=rotational viscosity
$A_C$=area of the liquid crystal
$P_S$=spontaneous polarization
$V_P$=drive voltage at $I_P$
d=cell thickness
$I_P$=measured peak current Viscosity is expressed in milli-Pascal*second.

This measurement is particularly sensitive to the quality of the alignment. Certain geometries, such as quasi-bookshelf, are known to give higher viscosity.

Specific Resistivity

The specific resistivity is found using the following formula $$p = A_C * \frac{R_M * R_P}{(R_M - R_P) * d}$$

where
p=specific resistivity
$A_C$=area of the liquid crystal
$R_M$=measured test cell resistance
$R_P$=measured parasitic resistance
d=cell thickness The specific resistivity is expressed in ohm*centimeter.

Threshold Voltage

The threshold voltage is a measured quantity. It is measured at a user specified percentage above the lower inflection point of the capacitance verses voltage curve. The default percentage is 5%.

Parallel Dielectric Constant

The parallel dielectric constant is determined as $$\varepsilon_{PAR} = \frac{C_{PAR}}{C_{EMPTY}}$$

where
$\in_{PAR}$=parallel dielectric constant
$C_{PAR}$=capacitance at $V_{th}/V_{rms}$=0 as extrapolated from a normalized threshold voltage versus cell capacitance plot.
$C_{EMPTY}$=measured empty cell capacitance The parallel dielectric constant has no units.

Perpendicular Dielectric Constant

The perpendicular dielectric constant is determined as $$\varepsilon_{PERP} = \frac{C_{PERP}}{C_{EMPTY}}$$

where
$\in_{PERP}$=perpendicular dielectric constant
$C_{PERP}$=measured capacitance at V<<$V_{th}$
$C_{EMPTY}$=measured empty cell capacitance The perpendicular dielectric constant has no units.

Dielectric Delta

The dielectric delta is the difference between the parallel and perpendicular dielectric constants as given by $\Delta\in=\in_{PAR}-\in_{PERP}$
$\Delta\in$=dielectric delta
$\in_{PAR}$=parallel dielectric constant
$\in_{PERP}$=perpendicular dielectric constant $K_{11}$ The splay elastic constant ($K_{11}$) is determined using the equation $$K_{11} = \left(\frac{V_{th}}{\pi}\right)^2 * \frac{\varepsilon_0 * \Delta\varepsilon}{\sqrt{3}}$$

where
$K_{11}$=splay elastic constant
$V_{th}$=threshold voltage
$\in_0$=dielectric constant=8.85e−12 Farads/meter
$\Delta\in$=dielectric delta $K_{22}$ The twist elastic constant ($K_{22}$) is estimated as 0.6*$K_{11}$.

$K_{33}$

The bend elastic constant ($K_{33}$) is obtained from curve fitting algorithm of the CV curve.

$K_{33}/K_{11}$

The ratio of the bend to splay constant is found as $K_{33}/K_{11}$.

Rotational Viscosity

The nematic rotational viscosity is calculated using the following equation $$\eta = A_C * \frac{(\varepsilon_0 * \Delta\varepsilon)^2}{2 * I_P} * \left(\frac{V_P}{d}\right)^3$$

where
$\eta$=rotational viscosity
$A_C$=area of the liquid crystal
$\in_0$=dielectric constant=8.85e−12 Farads/meter
$\Delta\in$=dielectric delta
$I_P$=measured peak current
$V_P$=drive voltage at $I_P$
d=cell thickness Viscosity is expressed in milli-Pascal*second.

This calculation is based on the high voltage limit as described in Jpn. J. Appl. Phys. 33. L119 (1994).

Ion Density

The ion density is calculated as $$ionDensity = \frac{q}{e * A_C * d}$$

where
ionDensity=positive or negative ion density
q=measured charge
e=electron charge=1.6022e−19 Coulombs
$A_C$=cell area
d=cell thickness Example Instrument The methods described can be used with any suitable instrument, as known in the art. The following description provides one embodiment of a suitable instrument.

In one embodiment, provided is an Automated Liquid Crystal Analysis System (LCAS) instrument, which is a fully automated system in one embodiment, consisting of hardware and software, for measuring the physical parameters of liquid crystal materials, of which nematic and ferroelectric are examples. In one embodiment, the hardware portion of the system consists of a Windows based computer, a PCI parallel interface card, and an electronic instrument that comprises, and in one embodiment, comprises the following: a waveform generator used to drive the LC cell, a bridge to measure the capacitive and resistive currents through the LC cell, and an integrator to measure total polarization charge after capacitive, resistive, and noise currents have been suppressed. The above may be housed in different enclosures, with the more preferable option being one enclosure. All aspects of the hardware are under software control and accessible to the user. The software portion of the system comprises, and in one embodiment, consists of, an on-screen menu bar to facilitate user interaction, the driver routines which interpret the user's key presses and send the appropriate control signals to the hardware, and an on-screen oscilloscope display to monitor the real-time input and output of the LC cell while measuring the resistance and capacitance of the LC cell.

In one embodiment, provided as a part of the LCAS is an automated dielectric spectrometer which measures the properties of a dielectric medium by first providing an electrical stimulus, and then reading back the signal, either capacitive, or optically. In one embodiment, the instrument can be connected to a host computer using only one cable. In one embodiment, the instrument is connected to a host computer using a PCI connection. In one embodiment, the instrument is connected to a host computer using a USB connection. In one embodiment, the instrument measures both optical and electrical signals. In one embodiment, the instrument contains software that allows convenient interface with existing software, such as Lab View, or a spreadsheet or word processing program. In one embodiment, the software is graphically based. In one embodiment, one or more of Electrical Rise time, Optical Rise time, Bistability, Specific Resistivity, Dielectric Constant are measured. In one embodiment, one or more of Splay elastic constant, Bend elastic constant, Dielectric anisotropy, Perpendicular dielectric constant, Parallel dielectric constant, Threshold voltage, VHR, residual DC voltage are measured. Other parameters may be measured. In one embodiment, there is an analog dial that adjusts the voltage applied to the cell. In one embodiment, there is a safety feature preventing shock by automatically shutting down the system when more than a specified current is detected, for example, >50 milliamps. In one embodiment, the instrument uses an arbitrary waveform generator to provide slow (0.001 Hz-30 KHz) triangle wave, either balanced or DC offset. In one embodiment, the waveform is one or more of the following: square wave, triangle wave, offset triangle wave, DC level, sine wave, dual pulse wave, and any symmetrical arbitrary wave. The frequency range is from 0.001-30 Hz in one embodiment, and the voltage output is up to 120 Vp in one embodiment. In one embodiment, the instrument uses an ultra-low noise voltage amplifier to measure the very high resistivity. In one embodiment, the instrument uses a three or four wire cell clip, allowing for minimization of noise. In one embodiment, the instrument automatically calculates the statistics of the LC cell. In one embodiment, the instrument automatically calibrates the system based on a known standard. In one embodiment, the output is captured as jpg or tab delimited data such as Excel format. In one embodiment, the LC properties can be optionally scanned vs. temperature affording the appropriate data, which can be presented as graphs. This feature can be implemented with the provide VHR coolNhot box, a hot stage with a range of −20 to +120° C., for example. The LCAS can also be interfaced with any commercial hot stage, for example, Instecc, Mettler, Linkam and others, where the temperature range can be as broad as −196 to +350° C.

In one embodiment, the system is controlled using a graphical user interface. In one embodiment, the applied drive signal is displayed, and the real time current or voltage response of the test cell to the applied signal is displayed. In one embodiment, the amplitude, frequency and applied waveform type can be selected using the graphical user interface.

In additional embodiments, a voltage holding ratio (VHR) coolNhot box is described for measurement of the voltage holding ratio and residual DC of the nematic LC cell using a voltage-based amplifier. This box is integrated into a Peltier stage allowing all properties to be measured in this enclosure from about −20 C to about +120° C., for example. The box can be either cooled by air with a fan, or if lower noise level is desired, a liquid cooling system can be used. In one embodiment, it is desired that the box is an enclosed system that does not require the use of an external water supply.

In the case of the nematic LC, for example, a C vs. V curve is automatically measured and the primary nematic properties are then calculated from this information, using the methods and techniques described herein.

REFERENCES

1. Patel, et al., Chem. Phys. Lett. 137, 91 (1987).
2. Dahl, et al. Phys. Rev. A 36, 4380 (1987).
3. Gouda et al., J. Appl. Phys. 67, 180 (1990).
4. Escher, et al. Liquid Crystals 3, 467 (1988).
5. Wu et al., Liquid Crystals 10, 635-646 (1991).
6. Imai et al. Jpn. J. Appl. Phys. 33, L119 (1994).

One of ordinary skill in the art will appreciate that methods, device elements and parameters other than those specifically exemplified can be employed in the practice of the invention without resort to undue experimentation. All art-known functional equivalents, of any such methods, device elements, and parameters are intended to be included in this invention. Whenever a range is given in the specification, for example, a temperature range, a time range, or a voltage range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein. The invention may also be practiced with the inclusion of components that are known in the art, such as electrical components that are not specifically mentioned here.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention. All references are incorporated by reference to the extent not inconsistent with the disclosure herewith.

In general the terms and phrases used herein have their art-recognized meaning, which can be found by reference to standard texts, journal references and contexts known to those skilled in the art.

Although the description herein contains many specificities, these should not be construed as limiting the scope of the invention, but as merely providing illustrations of some of the embodiments of the invention. Thus, additional embodiments are within the scope of the invention.

I claim:

1. A method for measuring physical properties of liquid crystals comprising:
    1. Providing a liquid crystal cell with a sample;
    2. Ramping the liquid crystal cell to the desired temperature;
    3. Applying a voltage to the sample in a predetermined pattern;
    4. Balancing the capacitance and resistance of the cell against a known value, thereby nulling the cell, to obtain the capacitance and resistance of the LC; or
    5. Alternatively, using quadrature with cosine stimulation to measure LC capacitance, independent of resistance;
    6. Increasing the value of the voltage in a periodic stepwise fashion to a next value;
    7. Repeating steps (3 and 4) or (3 and 5) until a CV curve is obtained at one temperature value;
    8. Determining the relationship between the theoretical and experimental CV curve through statistical analysis such as least squares fit to generate more accurate values of the elastic and dielectric constants;
    9. Increasing the temperature to the next desired increment (higher or lower) and repeating steps 3 through 8;
    10. Determining the liquid crystal transition temperature by scanning the temperature vs. capacitance and noting the change in the slope of the C vs. T curve to mark each liquid crystal transition;
    11. Repeating steps 3-8 until all desired physical properties have been obtained;
    12. Performing statistical analysis of multiple measurements of the same cell, or same measurement of multiple cells to generate statistical results including one or more of mean, standard deviation, variance, minimum, maximum, and the range of the specified set of LC cell or cells.

2. The method of claim 1, wherein the physical properties are one or more of: capacitance, resistance, thickness, Threshold voltage, Parallel dielectric constant, Perpendicular dielectric constant, Dielectric anisotropy, Splay elastic constant ($K11$), Twist elastic constant ($K2$), Bend elastic constant ($K33$), VHR (voltage holding ratio), Residual DC voltage, Polarization, Viscosity, Electrical Rise time, Optical Rise time, Bistability, Specific Resistivity, critical pulse width, ion density and Dielectric Constant.

3. The method of claim 1, wherein the voltage is a voltage waveform.

4. The method of claim 1, wherein the capacitance of the liquid crystal sample is measured as a predetermined heating or cooling temperature profile is automatically applied to the sample, generating capacitance v. temperature data, and wherein the desired result is the temperature at which a first or second derivative of the capacitance v. temperature data occurs.

5. The method of claim 4, wherein the desired result is a phase transition temperature.

6. The method of claim 1, wherein the determining step is performed more than once and statistical analysis is used to generate the result.

7. The method of claim 1, wherein the capacitance is measured by the null method.

8. The method of claim 1, wherein the capacitance is measured by applying a sine wave to the liquid crystal; measuring the current from the cosine and determining the capacitance.

* * * * *